(12) United States Patent
Woehr

(10) Patent No.: US 11,612,722 B2
(45) Date of Patent: Mar. 28, 2023

(54) NEEDLE ASSEMBLY AND COMPONENTS THEREOF

(71) Applicant: B. Braun Melsungen AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 16/174,007

(22) Filed: Oct. 29, 2018

(65) Prior Publication Data

US 2019/0060617 A1    Feb. 28, 2019

Related U.S. Application Data

(63) Continuation of application No. 15/269,583, filed on Sep. 19, 2016, which is a continuation of application No. 14/638,720, filed on Mar. 4, 2015, now Pat. No. 10,376,677, which is a continuation of application No. 14/286,756, filed on May 23, 2014, now Pat. No. 9,387,307, which is a continuation of application No. 13/842,968, filed on Mar. 15, 2013, now Pat. No. 8,784,387, which is a continuation of application
(Continued)

(51) Int. Cl.

| | |
|---|---|
| A61M 25/00 | (2006.01) |
| A61M 25/06 | (2006.01) |
| A61M 5/32 | (2006.01) |
| A61M 5/158 | (2006.01) |

(52) U.S. Cl.
CPC ........ *A61M 25/0618* (2013.01); *A61M 5/158* (2013.01); *A61M 5/3273* (2013.01); *A61M 25/0606* (2013.01); *A61M 2005/325* (2013.01)

(58) Field of Classification Search
CPC ........ A61M 5/3257; A61M 2005/3247; A61M 5/3271; A61M 25/0618; A61M 5/3243; A61M 5/1626; A61M 5/3273; A61M 5/50; A61M 5/321
See application file for complete search history.

(56) References Cited

U.S. PATENT DOCUMENTS

| | | |
|---|---|---|
| 3,610,240 A | 10/1971 | Harautuneian |
| 3,904,033 A | 9/1975 | Haerr |
| (Continued) | | |

FOREIGN PATENT DOCUMENTS

| | | |
|---|---|---|
| CN | 1589917 A | 3/2005 |
| CN | 101415456 A | 4/2009 |
| (Continued) | | |

OTHER PUBLICATIONS

Prior art drawings by B. Braun Medical, Inc., listed as "Ga. Spring Clip Detail for Introcan Catheter," ref. Nos. PRE-670 and PRE-671, on sale as early as Mar. 2000 (4 sheets).
(Continued)

*Primary Examiner* — William R Carpenter
(74) *Attorney, Agent, or Firm* — KOS IP Law LLP

(57) ABSTRACT

Needle assemblies are generally discussed herein with particular discussions extended to needle assemblies having a tip protector with a plurality of wall surfaces for preventing contact with the needle tip from a side. Aspects of the tip protectors discussed herein include a first protector body having an arm for blocking a needle tip surrounded by a second protector body having a plurality of wall surfaces.

21 Claims, 4 Drawing Sheets

Related U.S. Application Data

13/604,089, filed on Sep. 5, 2012, now Pat. No. 8,460,249, which is a continuation of application No. 11/496,769, filed on Jul. 31, 2006, now Pat. No. 8,382,718.

(56) References Cited

U.S. PATENT DOCUMENTS

| | | | |
|---|---|---|---|
| 4,160,450 | A | 7/1979 | Doherty |
| 4,725,267 | A | 2/1988 | Vaillancourt |
| 4,735,618 | A | 4/1988 | Hagen |
| 4,747,831 | A | 5/1988 | Kulli |
| 4,790,828 | A | 12/1988 | Dombrowski et al. |
| 4,795,432 | A | 1/1989 | Karczmer |
| 4,846,809 | A | 7/1989 | Sims |
| 4,929,241 | A | 5/1990 | Kulli |
| 4,944,725 | A | 7/1990 | McDonald |
| 4,952,207 | A | 8/1990 | Lemieux |
| 4,964,854 | A | 10/1990 | Luther |
| 4,978,344 | A | 12/1990 | Dombrowski et al. |
| 4,994,041 | A | 2/1991 | Dombrowski et al. |
| 5,049,136 | A | 9/1991 | Johnson |
| 5,051,109 | A | 9/1991 | Simon |
| 5,053,107 | A | 10/1991 | Barber, Jr. |
| 5,085,648 | A | 2/1992 | Purdy et al. |
| 5,126,090 | A | 6/1992 | Egolf et al. |
| 5,135,504 | A | 8/1992 | McLees |
| 5,147,327 | A | 9/1992 | Johnson |
| 5,171,229 | A | 12/1992 | McNeil et al. |
| 5,183,468 | A | 2/1993 | McLees |
| 5,215,528 | A * | 6/1993 | Purdy .............. A61M 5/3273 604/164.08 |
| RE34,416 | E | 10/1993 | Lemieux |
| 5,279,570 | A | 1/1994 | Dombrowski et al. |
| 5,312,371 | A | 5/1994 | Dombrowski et al. |
| 5,322,517 | A | 6/1994 | Sircom et al. |
| 5,328,482 | A | 7/1994 | Sircom et al. |
| 5,334,158 | A | 8/1994 | McLees |
| 5,344,408 | A | 9/1994 | Partika |
| 5,370,623 | A | 12/1994 | Kreamer |
| 5,423,766 | A | 6/1995 | Di Cesare |
| 5,501,675 | A | 3/1996 | Erskine |
| 5,558,651 | A | 9/1996 | Crawford et al. |
| 5,584,809 | A | 12/1996 | Gaba |
| 5,584,810 | A | 12/1996 | Brimhall |
| 5,584,818 | A | 12/1996 | Morrison |
| 5,599,310 | A | 2/1997 | Bogert |
| 5,601,536 | A | 2/1997 | Crawford et al. |
| 5,611,781 | A | 3/1997 | Sircom et al. |
| 5,662,610 | A | 9/1997 | Sircom |
| 5,697,907 | A | 12/1997 | Gaba |
| 5,718,688 | A | 2/1998 | Wozencroft |
| 5,738,665 | A | 4/1998 | Caizza et al. |
| 5,879,337 | A | 3/1999 | Kuracina et al. |
| 6,001,080 | A | 12/1999 | Kuracina et al. |
| 6,004,294 | A | 12/1999 | Brimhall et al. |
| 6,117,108 | A | 9/2000 | Woehr et al. |
| 6,287,278 | B1 | 9/2001 | Woehr et al. |
| 6,595,954 | B1 | 7/2003 | Luther et al. |
| 6,595,955 | B2 | 7/2003 | Ferguson et al. |
| 6,616,630 | B1 * | 9/2003 | Woehr .............. A61M 5/3273 604/110 |
| 6,623,458 | B2 * | 9/2003 | Woehr .............. A61M 5/3273 604/192 |
| 6,652,486 | B2 | 11/2003 | Bialecki et al. |
| 6,749,588 | B1 | 6/2004 | Howell et al. |
| 7,264,613 | B2 | 9/2007 | Woehr et al. |
| 7,753,877 | B2 | 7/2010 | Bialecki et al. |
| 8,162,904 | B2 | 4/2012 | Takano et al. |
| 8,460,249 | B2 | 6/2013 | Woehr |
| 2001/0027298 | A1 | 10/2001 | Vojtasek |
| 2001/0029356 | A1 | 10/2001 | Vojtasek |
| 2002/0026154 | A1 | 2/2002 | Chang |
| 2002/0169418 | A1 * | 11/2002 | Menzi .............. A61M 25/0637 604/164.07 |
| 2003/0060771 | A1 | 3/2003 | Bialecki et al. |
| 2003/0100868 | A1 | 5/2003 | Ferguson et al. |
| 2003/0105431 | A1 | 6/2003 | Howell |
| 2003/0195471 | A1 | 10/2003 | Woehr et al. |
| 2004/0049155 | A1 | 3/2004 | Schramm |
| 2004/0162522 | A1 | 8/2004 | Woehr |
| 2004/0204681 | A1 | 10/2004 | Thoresen et al. |
| 2004/0236288 | A1 | 11/2004 | Howell et al. |
| 2005/0027263 | A1 * | 2/2005 | Woehr .............. A61M 5/3273 604/263 |
| 2005/0027268 | A1 | 2/2005 | Qin et al. |
| 2005/0075609 | A1 * | 4/2005 | Latona .............. A61M 25/0618 604/164.08 |
| 2005/0096592 | A1 | 5/2005 | Carlyon et al. |
| 2005/0182362 | A1 * | 8/2005 | Sircom .............. A61M 5/3275 604/110 |
| 2005/0182363 | A1 | 8/2005 | Kulli |
| 2006/0074384 | A1 | 4/2006 | Kohler |
| 2006/0116638 | A1 | 6/2006 | Woehr et al. |
| 2007/0038183 | A1 | 2/2007 | Bialecki et al. |
| 2007/0038188 | A1 | 2/2007 | Bialecki et al. |

FOREIGN PATENT DOCUMENTS

| | | |
|---|---|---|
| EP | 0 408 290 | 1/1991 |
| EP | 0 434 324 | 6/1991 |
| EP | 0 449 510 | 10/1991 |
| EP | 1344544 | 9/2003 |
| EP | 1421969 | 5/2004 |
| EP | 1250943 B1 | 9/2004 |
| EP | 1886710 | 2/2008 |
| JP | 2001-514943 | 9/2001 |
| JP | 2002085558 | 3/2002 |
| JP | 2003-180833 | 7/2003 |
| JP | 2004-113394 | 4/2004 |
| JP | 2005-529717 | 10/2005 |
| JP | 2005-533617 A1 | 11/2005 |
| MX | 209311 | 10/1997 |
| WO | WO 99/08742 | 2/1999 |
| WO | WO 01/10488 | 2/2001 |
| WO | WO 01/93940 | 12/2001 |
| WO | WO-0193940 A2 * | 12/2001 ........ A61M 25/0625 |
| WO | WO 2004/000408 A1 | 12/2003 |
| WO | WO 2004/093961 | 11/2004 |
| WO | WO 2005042080 A1 | 5/2005 |
| WO | WO 2005/079891 | 9/2005 |
| WO | WO 2006/062983 A1 | 6/2006 |
| WO | WO 2007/122958 | 11/2007 |

OTHER PUBLICATIONS

Information Disclosure Statement (IDS) of Reissue Application Patent No. 6,652,486 B2, Issued Nov. 25, 2003, Express Mail No. EV425513038US, including Substitute Form PTO-1449, cited for U.S. Appl. No. 11/013,289 (6 pages).

International Search Report completed Dec. 12, 2007 and dated Dec. 21, 2007 from related PCT Application No. PCT/EP2007/006571, filed Jul. 24, 2007 (6 pages).

English translation of Office Action on corresponding foreign application (BR Application No. BR122013013981-8) from the Brazilian Patent Office dated Apr. 17, 2018.

English translation of Office Action on corresponding foreign application (BR Application No. PI0714954-9) from the Brazilian Patent Office dated Apr. 17, 2018.

Office Action on corresponding foreign application (CN Application No. 200780036689.1) from the State Intellectual Property Office dated Dec. 27, 2010.

English translation of the Office Action dated Apr. 23, 2013 from related Chinese Application No. 201210085005X (3 pages).

Office Action on corresponding foreign application (CN Application No. 201210085004.5) from the State Intellectual Property Office dated Dec. 19, 2013.

Extended European Search Report dated May 22, 2013 from related European Application No. 13157472.5 (7 pages).

Extended European Search Report dated Aug. 23, 2016 from related European Application No. 16164681.5 (13 pages).

(56) References Cited

OTHER PUBLICATIONS

Opposition against European Patent No. 2604308—Notice of Opposition; Apr. 29, 2015.
Opposition against European Patent No. 2604308⇒Response to the opposition; Jul. 18, 2016.
Opposition against European Patent No. 2604308—Response to the observations filed by the patentee; Oct. 12, 2016.
Opposition against European Patent No. 2604308—Response to the submission of the Opponent; Dec. 9, 2016.
Opposition against European Patent No. 2604308—Additional submission on the accelerated processing of the present opposition proceedings; Dec. 19, 2016.
Opposition against European Patent No. 2604308—Response to observations and additional submission filed by the patentee; Feb. 17, 2017.
Opposition against European Patent No. 2604308—Response to Summons; Jul. 6, 2017.
Opposition against European Patent No. 2604308—Response to the preliminary opinion of the Opposition Division, annexed to the summons to oral proceedings; Jul. 14, 2017.
Opposition against European Patent No. 2604308—Written Submission on preparation to oral proceedings; Sep. 14, 2017.
Opposition against European Patent No. 2604308—Interlocutory decision on Opposition proceedings and Minutes of the oral proceedings before the Opposition Division; Dec. 12, 2017.
Opposition against European Patent No. 2604308—Opponent's grounds of appeal; Apr. 12, 2018.
Opposition against European Patent No. 2604308—Response to the grounds of appeal of the appellant; Aug. 22, 2018.
Examiner's Report on corresponding foreign application (IN Application No. 500/DELNP/2009) from the Indian Intellectual Property Office dated May 31, 2017.
Office Action on corresponding foreign application (JP Application No. 2009-522142) from the Japan Patent Office dated Mar. 12, 2012.
Office Action on corresponding foreign application (JP Application No. 2012-200176) from the Japan Patent Office dated Nov. 5, 2013.
Office Action on corresponding foreign application (JP Application No. 2012-200177) from the Japan Patent Office dated Nov. 5, 2013.
English translation of Rejection Decision on corresponding foreign application (TW Application No. 096125332) from the Taiwanese Patent Office dated Sep. 24, 2013.
Office Action dated Jul. 9, 2008 from corresponding U.S. Appl. No. 11/496,769.
Final Office Action dated Dec. 12, 2008 from corresponding U.S. Appl. No. 11/496,769.
Office Action dated May 8, 2009 from corresponding U.S. Appl. No. 11/496,769.
Final Office Action dated Aug. 31, 2009 from corresponding U.S. Appl. No. 11/496,769.
Examiner's Answer dated Apr. 12, 2010 from corresponding U.S. Appl. No. 11/496,769.
Office Action dated Dec. 5, 2012 from corresponding U.S. Appl. No. 13/604,089.
Non-Final Office Action on co-pending U.S. Appl. No. 14/286,756 dated Nov. 19, 2015.
Non-Final Office Action on co-pending U.S. Appl. No. 14/638,720 dated Jan. 12, 2017.
Final Office Action on corresponding foreign application (BR Application No. 12 2013 013981-8) from the Brazilian Patent Office dated Oct. 5, 2018.
Office Action on co-pending U.S. Appl. No. 15/269,583 dated Mar. 20, 2020.
First Office Action on corresponding foreign application (CN Application No. 201210085004.5) from the Chinese Patent Office dated Jul. 3, 2013.
Third Office Action on corresponding foreign application (CN Application No. 201210085004.5) from the Chinese Patent Office dated Jun. 10, 2014.
First Office Action on corresponding foreign application (EP Application No. 13 157 472.5) from the European Patent Office dated Apr. 30, 2014.
Office Action on corresponding foreign application (EP Application No. 13 157 472.5) from the European Patent Office dated Feb. 13, 2015.
Second Office Action on corresponding foreign application (JP Application No. 2009-522142) from the Japanese Patent Office dated Apr. 2, 2013.
Final Office Action on corresponding foreign application (JP Application No. 2012-200176) from the Japanese Patent Office dated Aug. 12, 2014.
Final Office Action on corresponding foreign application (JP Application No. 2012-200177) from the Japanese Patent Office dated Sep. 2, 2014.
Final Office Action on co-pending U.S. Appl. No. 15/269,583 dated Nov. 4, 2019.
Office Action on co-pending U.S. Appl. No. 15/269,583 dated Aug. 10, 2020.
First Examination Report on corresponding foreign application (IN Application No. 201818004089) from the Indian Patent Office dated May 10, 2021.

* cited by examiner

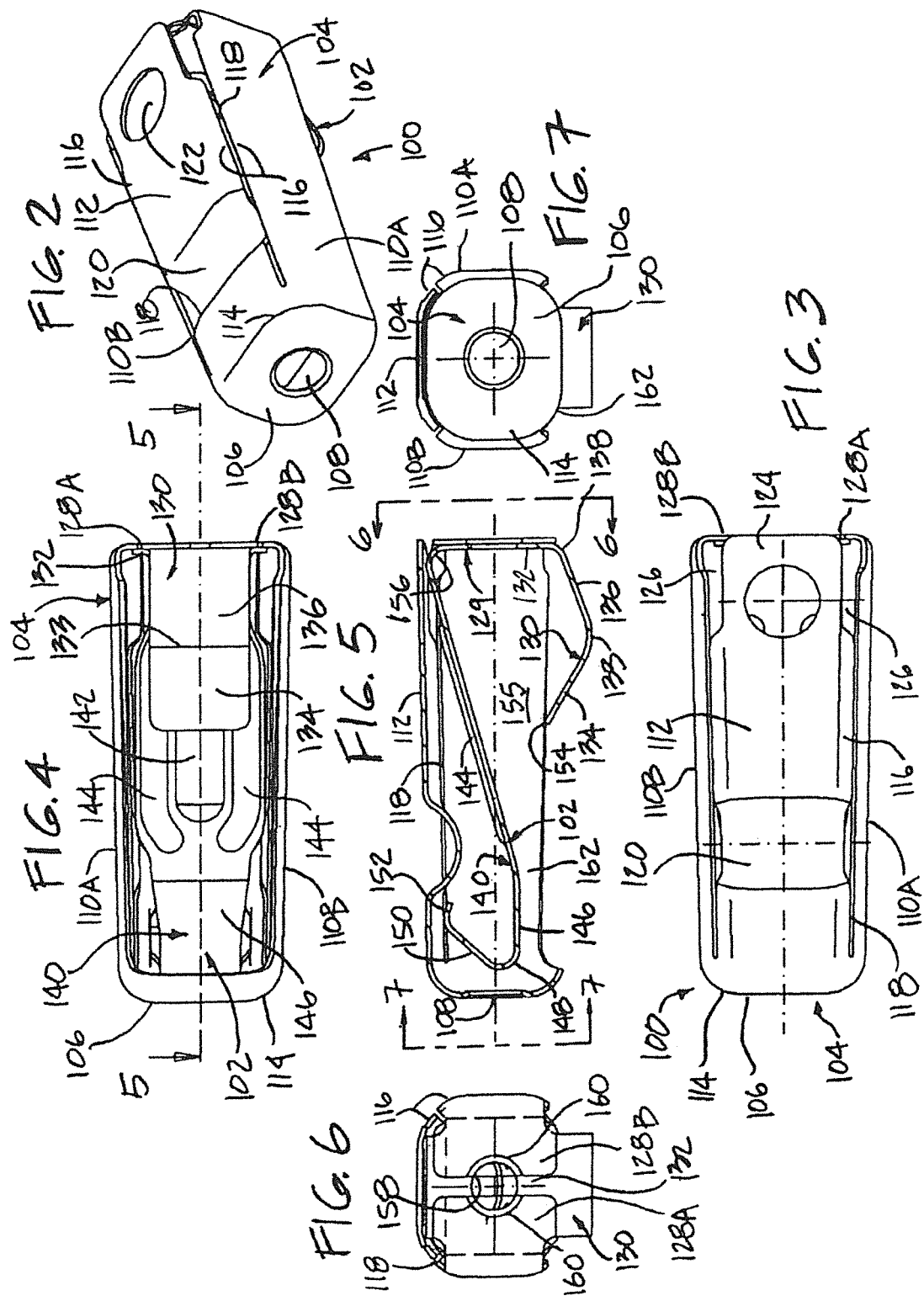

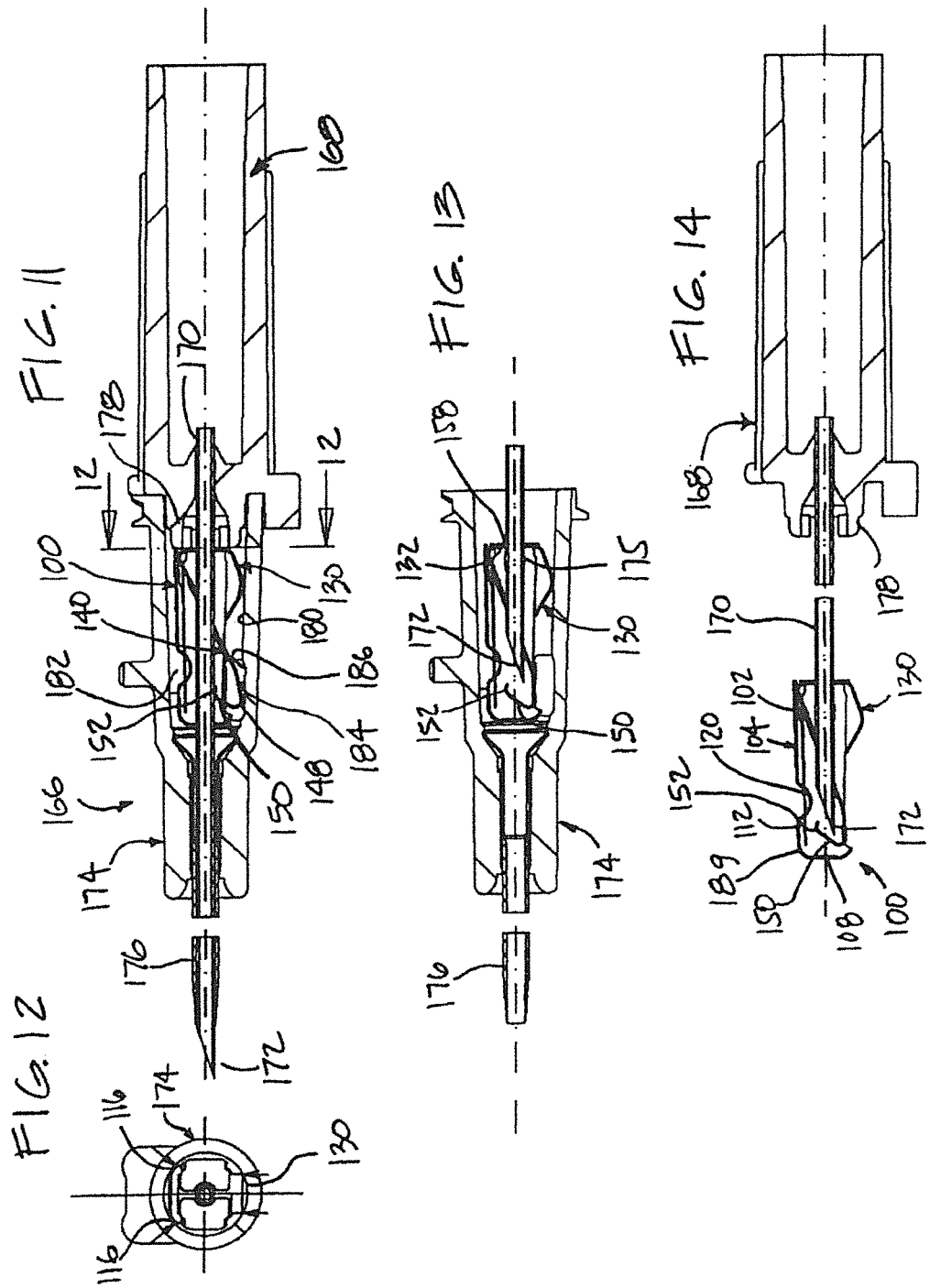

NEEDLE ASSEMBLY AND COMPONENTS THEREOF

CROSS-REFERENCE TO RELATED APPLICATION

This is a continuation of application Ser. No. 15/269,583, filed Sep. 19, 2016, the contents of which are expressly incorporated herein by reference.

FIELD

Needle assemblies are generally discussed herein with particular discussions extended to needle assemblies having a tip protector comprising enclosed wall surfaces for preventing contact with the needle tip from a side.

BACKGROUND

Insertion procedure for an IV catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand; and (4) the healthcare worker then tapes the now inserted catheter to the patient's skin and connects the exposed end of the catheter (the catheter hub) to the source of the fluid to be administered into the patient's vein.

The problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. For the period between placing the used needle on a tray or a work station to the time it is discarded, the used needle is a potential source for disease transmissions for those that work near or around the needle. Accordingly, all needles should be covered immediately following use to ensure greater worker safety. Ideally, the procedure for covering the needle tip should be passive, self activating, or at least simple to perform. In addition, the device for covering the needle should be reliable and robust.

SUMMARY

In accordance with aspects of the present invention, a tip protector is provided that blocks the needle tip from direct contact with a needle tip.

More preferably, the tip protector incorporates side walls for providing shielding the needle tip from view and exposure to blood dripping from the inside of the needle tip.

In a further aspect of the present invention, a deflector plate is provided to deflect the needle from inadvertently re-emerging from within the tip protector.

In yet another aspect of the present invention, the deflector plate is used, at least in part, to position the tip protector within a housing.

It is another object of the present invention to incorporate the tip protector in a safety IV catheter for automatically shielding a needle tip upon removal of a needle from a catheter tube by means of a resilient engagement between the tip protector and the catheter hub. The resilient engagement allowing for a relatively smoother release without having to reduce typical manufacturing tolerances.

Aspects of the present invention may be practiced by providing a tip protector for blocking a needle tip comprising: a tip protector housing positioned inside a hub having an interior surface; a needle passing through the tip protector and the housing; a first arm extending from a distal wall of the tip protector housing biased against the interior surface; a second arm extending from a proximal wall of the tip protector housing biased against the interior surface; and a third arm extending from the proximal wall of the tip protector housing and biased against a side of the needle.

The present invention may also be practiced by providing a tip protector for mounting on a needle to shield a needle tip comprising: a first protector body comprising a proximal wall and an arm extending distally of the proximal wall; said arm further comprising: a distal wall at an end of the arm for blocking a needle tip; a non-uniform arm width for accommodating a needle extending from between the proximal wall and the distal wall; a second protector body attached to the first protector body, the second protector body comprising a distal wall and two side walls defining a cavity for accommodating the first protector body; and a deflector plate comprising a projection projecting into the cavity, the projection and the distal wall at the end of the arm are configured to limit movement of a needle tip from moving distally of the distal wall of the second protector body.

In yet another aspect of the present invention, there is provided a tip protector for mounting on a needle to shield a needle tip comprising: a first protector body attached to a second protector body; the first protector body comprising a proximal wall and an arm, which comprises a distal end portion of the arm, extending distally of the proximal wall; the second protector body comprising two side walls and two end walls defining a cavity for accommodating the first protector body; the two side walls each comprising a first edge and a second edge; a deflector plate comprising a projection projecting into the cavity, the deflector plate is configured to deflect and move relative to both the first edge and the second edge; and wherein the projection and the distal end portion of the arm are configured to be on different sides of a needle shaft defined by a centerline when the tip protector is mounted on a needle and the tip protector is in a ready to use position.

In still yet another aspect of the present invention, there is provided a needle assembly comprising: a housing comprising a wall having an interior wall surface defining a cavity having a tip protector disposed therein; a needle, which has a shaft having a first side and a second side defined by a centerline and a needle tip, passing through the housing and the tip protector; the tip protector comprising a distal wall, two side walls, a proximal wall, a first arm extending from the proximal wall towards the distal wall, a second arm, which is shorter than the first arm, extending from the proximal wall, and a wall opposite the second arm;

and wherein the wall opposite the second arm and the second arm are both biased against the interior wall surface of the housing.

Other aspects and features of the tip protectors provided herein may be better appreciated as the same become better understood with reference to the specification, claims, and appended drawings.

BRIEF DESCRIPTION OF THE DRAWINGS

The appended drawings include:

FIG. 2 is a semi-schematic perspective view of a tip protector provided in accordance with aspects of the present invention comprising a first protector body and a second protector body for blocking a needle tip;

FIG. 3 is a top view of the tip protector of FIG. 2;

FIG. 4 is a bottom view of the tip protector of FIG. 2;

FIG. 5 is a semi-schematic cross-sectional side view of the clip of FIG. 4 taken along line 5-5;

FIG. 6 is a semi-schematic end view of the clip of FIG. 5 taken along line 6-6;

FIG. 7 is a semi-schematic front view of the clip of FIG. 5 taken along line 7-7;

FIG. 11 is a semi-schematic cross-sectional side view of a catheter assembly incorporating the tip protector of FIG. 2 shown in a ready to use position;

FIG. 12 is a cross-sectional end view of the catheter assembly of FIG. 11 taken along line 12-12;

FIG. 13 is a partial cross-sectional side-view of the catheter assembly of FIG. 11 shown with the needle hub retracted from the catheter tube and the tip protector blocking the needle tip, in a used position;

FIG. 14 is a partial cross-sectional side view of the needle hub completely removed from the catheter hub with the tip protector of FIG. 2 remained on the needle for blocking the needle tip.

DETAILED DESCRIPTION

The detailed description set forth below in connection with the appended drawings is intended as a description of the presently preferred embodiments of a tip protector for use on a number of needles or needle assemblies provided in accordance with aspects of the present invention and is not intended to represent the only forms in which the present invention may be constructed or utilized. The description sets forth the features and the steps for constructing and using the tip protector of the present invention in connection with the illustrated embodiments. It is to be understood, however, that the same or equivalent functions and structures may be accomplished by different embodiments also intended to be encompassed within the spirit and scope of the invention, especially those incorporating a combination of features shown in the different embodiments included herein. As denoted elsewhere herein, like element numbers are intended to indicate like or similar elements or features.

Figure 1A:
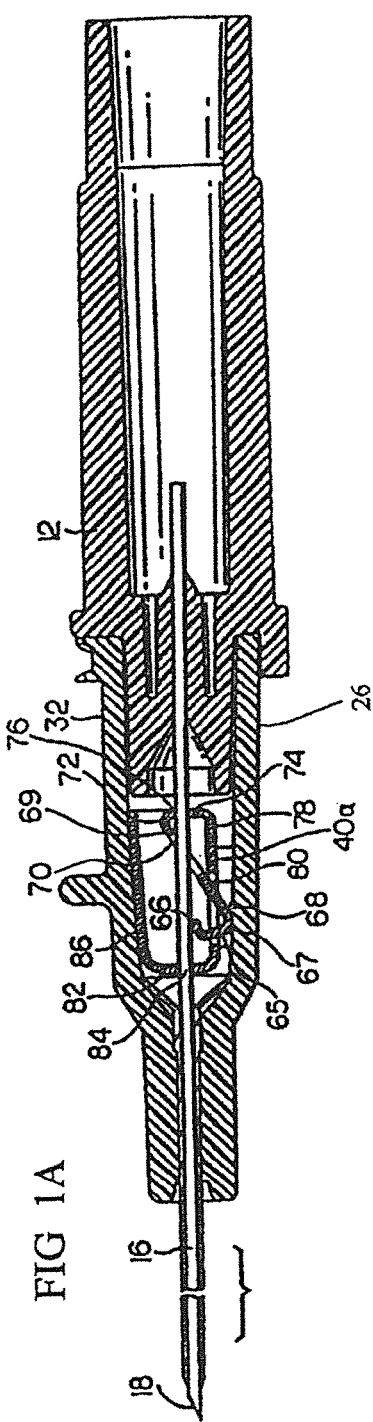
FIGS. 1A and 1B are semi-schematic views in partial cross-section of a prior art safety IV catheter incorporating a tip protector comprising an upper wall and two side walls.
Figure 1B:
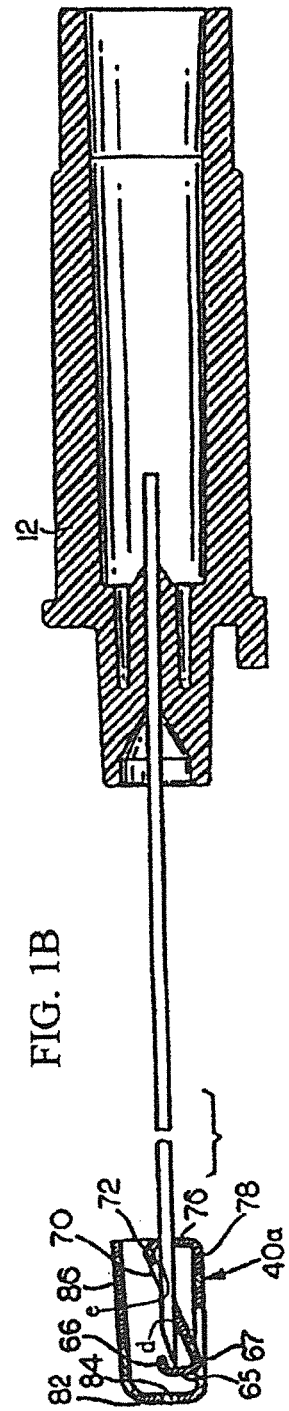

FIGS. 1A and 1B illustrate a prior art spring clip needle guard shown and described in U.S. Pat. No. 6,616,630 to Woehr et al., the contents of which are expressly incorporated herein by reference. For cross-referencing purposes, FIGS. 1A and 1B shown herein are labeled and discussed in the '630 patent as FIGS. 4A and 4B. As therein shown and reproduced above as FIGS. 1A and 1B, the spring clip needle guard 40a includes a distal arm 65 terminating at its upper end in a curved lip 66 and at its lower end in a U-shaped portion 67 which, in the ready position illustrated in FIG. 1A, contacts a bump 68 formed in the lower inner wall of the catheter hub 26.

A transverse segment 69 having a central opening 70 extends proximally and upwardly and terminates at an upper U-shaped portion 72. As disclosed in the '630 patent, the opening is configured to clamp the needle in a used position, at points d and e, which have been added. A proximal end wall 74 having an opening 76 extends vertically from portion 72 and then extends distally in a horizontal lower segment 78, which has an opening 80 through which the lower halves of the distal arm 65 and the transverse segment 69 extend in the ready position of the needle guard. Segment 78, at its distal end, extends upwardly at a front wall 82 which has a central opening 84 axially aligned with openings 70, 76. At its upper end, the distal front wall 82 extends in the proximal direction in an upper segment 86, which, as shown in FIG. 1A, contacts the upper inner wall of the catheter hub along substantially its entire length.

When the catheter is in the ready position, the needle shaft passes through openings 70, 76 and 84 and rests on the curved lip 66, which urges the arm 65 against the bump 68 in the lower wall of the catheter hub. That engagement, along with the resilient engagement of the upper segment 86 with the upper interior wall of the catheter hub, retains the spring clip 40a in its ready position within the catheter hub.

When the needle hub 12 and needle 16 are retracted to the right, as viewed in FIG. 1A, by a sufficient amount, the needle tip 18 moves proximal of the lip 66 and eventually passes below the lip 66. When this occurs, the downward force on the arm 65 releases thus allowing the arm 65 to snap upwards to the retracted position illustrated in FIG. 4B, in which the arm 65 and the lip 66 extend over the needle tip 18 to thereby prevent accidental contact with the needle tip. In this condition, the needle guard 40a is clamped onto the needle shaft 16 at points d and e of opening 70 and the needle and needle guard clamped thereto can be readily removed from the catheter hub.

While the prior art tip protector 40a shown in FIGS. 1A and 1B is well-designed for its intended purposes, there remains a number of improvements to the tip protector 40a that could be made to make it more reliable, effective, and easier to manufacture.

With reference now to FIG. 2, a tip protector provided in accordance with aspects of the present invention is shown, which is generally designated 100. In one exemplary embodiment, the tip protector 100 comprises a first protector body (See, also FIG. 5) 102 surrounded, at least in part, by a second protector body 104.

In one embodiment, the second protector body 104 comprises a distal wall 106 comprising an opening 108, which is preferably circular in configuration. A plurality of walls extend distally of the distal wall 106, which include two side walls 110A, 110B and a deflector wall, plate, or arm 112. The second protector body 104 is preferably formed from a single stamped or cut-out stainless steel sheet resembling a "T", which has a circular cut-out 108 at the intersection of the three branches of the "T" for forming the opening 108 on the distal wall 106. In one exemplary embodiment, the intersection of the T-shape sheet is pressed against a metal form or die, such as carbide, which then forms the curvilinear perimeter contour 114 around the perimeter of the distal wall 106 while concurrently pushing the two side walls 110A, 110B and the deflector plate 112 proximally. A bottom perimeter contour can also formed by this process.

In one exemplary embodiment, the edges 116 of the two side walls 110A, 110B and the deflector plate 112 are formed fitted in the same die used to form the curvilinear perimeter contour 114 of the distal wall 106. Thus, the intersections 118 between the two side walls 110A, 110B and the deflector plate 112 are generally curved or smooth rather than at right angles (also shown in FIGS. 6 and 7). As further discussed below, the smooth edges 116 allow the tip protector 100 to contact an interior surface of a clip housing or catheter hub over a larger surface area as compared to corners having a simple right-angle, which would result in a single point contact. The side walls and deflector plate are preferably close enough together to shield the needle tip from view and catch any drop of blood that may drip from the needle while inside the needle tip.

In one exemplary embodiment, a projection or dimple 120 is incorporated on the deflector plate 112 for delimiting needle movement in an activated position, as further discussed below. The width of the dimple section 120, extending from one side wall 110A to another side wall 110B, is slightly less than the width of the deflector plate immediately proximally and distally of the dimple section. The dissimilar widths along the deflector plate 112 allow the dimple 120 to be formed following formations of the smooth corners 116. However, the tip protector 100 may incorporate right angle corners at the various intersections 118 and the deflector plate 112 having a uniform width, which are less preferred, without deviating from the spirit and scope of the present invention. An optional opening 122 may be incorporated on the deflector plate 112 for ease of assembly. For example a pin (not shown) could be inserted through the opening 122 to push the arm 140 (FIG. 5) of the first protector body downwards. This could assist in assembling the butt end of a cannula or needle through the protector. Preferably the opening is not necessary as the distal wall 150 of the first protector body 102 is formed at an angle thus allowing the butt end of the cannula to simply deflect the distal wall downwards for an automatic assembly.

FIG. 3 is a top view of the tip protector 100 of FIG. 2. In one exemplary embodiment, a reduced proximal section 124 is incorporated on the deflector plate 112, which has a smaller width dimension that the section immediately distally. A gap 126 is created on each side of the reduced proximal section 124, which is defined in part by each side wall 110A, 110B and the reduced proximal portion 124. The two gaps 126, however, can be filled by keeping the same width the entire length of the deflector plate 112.

In one exemplary embodiment, a side wall attachment plate 128A, 128B is incorporated at a proximal end of each side wall 110A, 110B. If a centerline or axis is drawn lengthwise of the tip protector 100, the two side wall attachment plates 128A, 128B are positioned orthogonally of the axis and are generally coplanar. However, the two attachment plates 128A, 128B can overlap and be non-coplanar without deviating from the spirit and scope of the present invention. As further discussed below, the two attachment plates 128A, 128B are means by which the second protector body 104 attaches to the first protector body 102.

FIG. 4 is a bottom view of the tip protector 100 of FIG. 2. The first protector body 102 is clearly shown positioned between the two side walls 110A, 110B of the second protector body 104. In one exemplary embodiment, an arm 130 for stabilizing the tip protector 100 within a housing or hub is incorporated. The arm 130 extends distally from a proximal wall 132 (See also FIG. 5) and includes a bend or apex 133 defined by an upstream section 134 positioned at an angle to a downstream section 136 (See also FIG. 5). The arm 130 has two ends. One of the two ends of the arm 130 is fixed and not movable and an opposite end that is a free end, which is not fixed and movable. As further discussed below, the arm 130 is configured to pivot, flex, or cantilevered about a point 138 at a proximal end of the tip protector 100, which acts like a hinge. The proximal wall 132 and the two attachment plates 128A, 128B together define a protector proximal end 129.

An arm 140, of relatively longer length than the arm 130 for stabilizing, for blocking a needle tip also extends from the proximal wall 132. In one exemplary embodiment, the arm 140 comprises an opening 142 and two ribs 144. Preferably, the opening 142 has an oblong shape and the two ribs 144 are formed by a coining process. The arm 140 further includes a forearm section 146, a return section 148 (FIG. 5), a distal wall 150 (FIG. 5) for blocking a needle tip, and an end section or finger 152 (FIG. 5) for overlapping a portion of the needle in the used position. Together, the forearm section 146, the return section 148, the distal wall 150, and the finger 152 are collectively referred to herein as a distal arm blocking section. The arm 140 has two ends. One of the two ends of the arm 140 is fixed and not movable and an opposite end that is a free end, which is not fixed and movable. The finger 152 and the distal wall 150 are at the free end of the arm 140. In one exemplary embodiment, the section of the arm with the opening 142 is wider than the remaining arm sections. This configuration provides room to not only incorporate the opening 142 but also the two coined ribs 144. Alternatively, a tab or flab may be incorporated on each edge of the arm section and then bending them to form two ribs. The alternative arm, without the coined ribs, may have a uniform width throughout.

FIG. 5 is a cross-sectional side view of the tip protector of FIG. 4 taken along line 5-5. The two arms 130, 140 can be seen extending from two different edges of the proximal wall 132. As shown in FIG. 11, when the tip protector 100 is positioned on a needle, the two arms originate from opposite side of the needle, viewed from a needle centerline. However, the longer arm 140 extends distally of the proximal wall 132 at an angle and transects the needle axis, with the needle passing through the opening 142 on the arm. The short arm 130, however, does not touch or intersect the needle. More preferably, the end edge 154 of the short arm 130 is spaced apart from the needle, both in a ready to use position and a used position.

As further discussed below, when the tip protector 100 is in a ready to use position, the long arm 140 is biased radially outwardly towards the short arm 130 and the finger 152 in contact with a side of the needle. To that end, the long arm 140 is flexed, at least in part, about a point 156 at the proximal wall 132 when in abutting contact with a side of the needle.

Referring again to FIG. 3 in combination with FIG. 5, the deflector plate 112 is cantilevered from the perimeter contour 114 of the distal wall 106 of the second protector body 104. This allows the whole deflector plate 112, and more specifically the reduced proximal portion 124, to deflect like a springboard. In one exemplary embodiment, the dimension between the apex 133 of the short arm 130 and the rounded edges 116 of the deflector plate 112 should be larger than the internal curvature of a housing the tip protector is to be placed into so that both the deflector plate 112 and the short arm 130 are biased inwardly by the wall surface of the housing. Said differently, when the tip protector 100 is mounted inside a housing, such as the catheter hub shown in FIG. 11, the tip protector is squeezed at the two rounded edges on the deflector plate 112 and the short arm 130. This squeezing action allows the tip protector to be removeably secured to the housing or hub.

FIG. 6 is an end view of the tip protector of FIG. 5 taken along line 6-6. The two side attachment plates 128A, 128B are shown in contact with the proximally facing surface of the proximal wall 132. In one exemplary embodiment, the two attachment plates 128A, 128B are welded, using ultrasound, high frequency welding, or laser, to the proximal wall 132. An opening 158 is incorporated on the proximal wall 132 of the first protector body 102 for receiving a needle (not shown). The two attachment walls 128A, 128B both incorporate cut-outs 160 resembling two semi-circles that together have a larger diameter than the opening 158 on the proximal wall 132. Alternatively, the two attachment walls 128A, 128B can overlap one another and each incorporating a separate opening having a larger diameter than the diameter on the opening 158 of the proximal wall.

FIG. 7 is a front view of the tip protector 100 of FIG. 5 taken along line 7-7. As clearly shown, the second protector body 104 incorporates a plurality of walled structures, namely the two side walls 110A, 110B and the deflector plate 112, a front wall 106, and two attachment walls 128A, 128B (not shown) to form an enclosure comprising a cavity 155 and a central access opening 162 (See also FIG. 5). With reference to FIGS. 5 and 6 in addition to FIG. 7, the short arm 130 projects out through the central access opening 162 to provide a contact point between the tip protector and a housing, such as a catheter hub. The long arm 140 (FIG. 5) similarly projects out through the central access opening 162 when in a ready-to-use position but moves into the cavity 155 when in a used position, as further discussed below.

Figure 8:
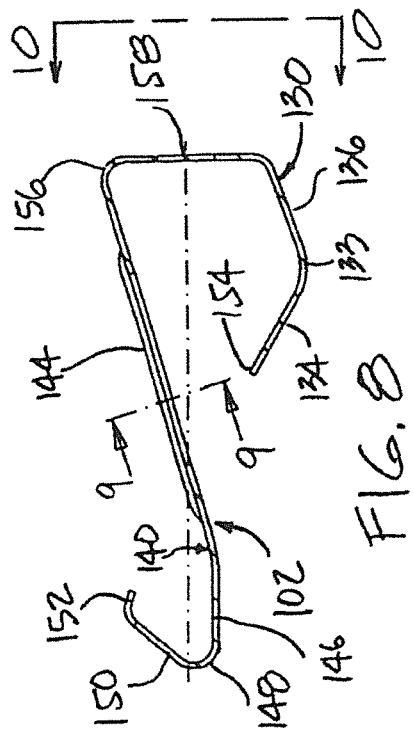
FIG. 8 is a semi-schematic cross-section side view of the first protector body of FIG. 2 shown without the second protector body.

FIG. 8 is a cross-sectional side view of the first protector body 102 of FIG. 1, shown without the second protector body 104. In one exemplary embodiment, the first protector body 102 is formed from an single integral stainless steel sheet. The opening 142 should be stamped and the two ribs 144 coined before the first protector body 102 is formed to the shape shown in FIG. 8.

Figure 9:
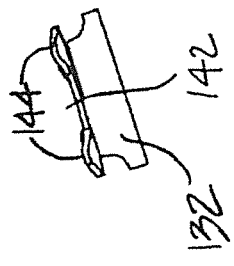
FIG. 9 is a semi-schematic cross-sectional end view of an arm of the first protector body of FIG. 8 taken along line 9-9.

FIG. 9 is a cross-sectional end view of the first protector body 102 of FIG. 8 taken along line 9-9. Part of the two ribs 144, the opening 142 between the two ribs, and the proximal wall 132 are shown.

Figure 10:
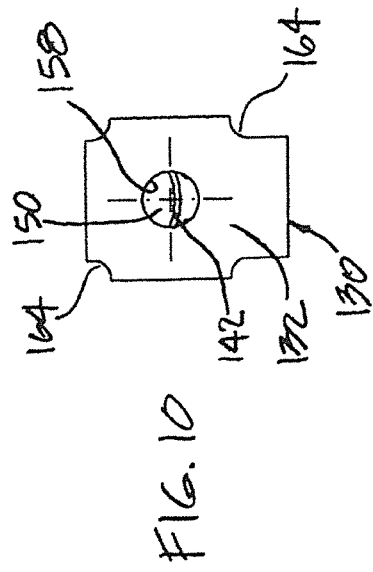
FIG. 10 is a semi-schematic end view of the first protector body of FIG. 8 taken along line 10-10.

FIG. 10 is an end view of the first body section 102 of FIG. 8 taken alone line 10-10. Part of the oblong opening 142 and the distal wall 150 can be seen through the opening 158 on the proximal wall 132. In one exemplary embodiment, four cut-outs 164 are formed at each corner of the proximal wall 132. The cut-outs 164 are configured to reduce the amount of spring force the two arms 130 and 140 generate. The amount of cut out can be varied to obtain a desired spring force.

With reference again to FIG. 5, the tip protector disclosed herein may be viewed as a device having a housing with three moveable arms 112, 130, and 140. The tip protector may also be viewed as having a housing with a deflector plate or arm with a tip protector disposed therein having an arm for blocking a needle tip and an arm, together with the deflector plate, for resiliently securing the tip protector to a hub or clip housing.

FIG. 11 is a semi-schematic cross-sectional side view of a catheter assembly 166 incorporating the tip protector 100 of FIGS. 2-10. Broadly speaking, the catheter assembly 168 comprises a needle hub comprising a needle 170 attached thereto. The needle 170 comprises a sharpened needle tip 172, a non-uniform needle section 175 (FIG. 13), and projects through the tip protector 100, the catheter hub 174, and the catheter tube 176. The non-uniform needle section 175 may be a crimp, a material build-up, a bend, or combinations thereof. In a preferred embodiment, the needle hub 168 incorporates a nose section 178 that projects into the interior wall surface 180 of the catheter hub 174. The nose section 178 is configured to push the protector proximal end 129 of the tip protector 100 to a desired depth or length inside the cavity 182 defined by the wall surface 180 of the catheter hub 174 in the ready to use position (FIG. 11).

In one exemplary embodiment, the cavity 182 includes a recessed section 184, which may extend the entire internal circumference of the cavity along a band or width or a partial circumference, as shown. The recessed section 184 provides added space for the distal end of the first body section 102 so as to reduce the amount of compression or biasing force on the finger section 152 and the return section 148. This in turn, reduces the drag between the finger section 152 and the side of the needle 170 during relative movement between the needle and the tip protector 100. Obviously, the needle assembly 166 may be practiced without the recessed section 184, but not as preferred.

As shown, the recessed section 184 comprises a proximal tapered section 186 and a distal tapered section. With reference to FIG. 5 in addition to FIG. 11, the forearm section 146, the return section 148, and the distal wall 150 of the first body section 102 are all positioned distally of and spaced apart from the proximal tapered section 186. The space apart configuration is incorporated as physical contact between the proximal tapered section 186 and the distal arm blocking section is not required to maintain a fixed relationship between the catheter hub 174 and the tip protector 100 during movement of the needle hub 168 relative to the catheter hub. However, contact between the two may be incorporated without deviating from the spirit and scope of the present invention.

Referring now to FIG. 12, which is a cross-sectional end view of the catheter assembly of FIG. 11 taken along line 12-12, the tip protector 100 is shown contacting the interior wall surface 180 of the catheter hub 174 at the two curbed edges 116 on the deflector plate 112 and two edges of the short arm 130, in the general area of the apex 133. The four contact points are shown in FIG. 12 with four contact arrows. Thus, in one exemplary embodiment, an arm 130 is cantilevered from a proximal end of the first protector body 102 and another arm 112 is cantilevered from a distal end of the second protector body 104 to retain the tip protector 100 within a catheter hub. Said differently, a tip protector is herein provided having an arm cantilevered from a proximal wall of a protector housing and a second arm cantilevered from a distal wall of the same protector housing. In an alternative embodiment, the cantilever arm 112 is eliminated and the two side walls 110A, 110B along with the short arm 130 are configured to removeably secure the alternative tip protector to a housing, such as a catheter hub or a clip housing.

FIG. 13 is a partial cross-sectional side view of the catheter assembly 166 of FIG. 11, shown in a used position, with the needle 170 retracted to the right of FIG. 11. The tip protector 100, hence the needle 170, is moved to the used position shown in FIG. 13 by holding the catheter hub 174 in one hand while withdrawing the needle hub 168 to the right of FIG. 11 (or vice-versa, i.e., holding the needle hub 168 while moving the catheter hub 174 to the left of FIG. 11). As the needle tip 172 moves proximally of the finger section 152, the biasing force acting on the arm 140 is removed thus allowing the arm to recoil to its less flexed state, which is shown in FIG. 13. As the needle hub 168 continues to move to the right, the non-uniform section 175 on the needle 170, which has a larger cross-sectional dimension than the opening 158 on the proximal wall 132 of the first protector body 102, contacts the opening 158 and pulls the proximal wall, via the engagement with the perimeter of the opening 158, to the right. If the pulling force on the proximal wall 132 is greater than the friction force between the cantilever arm 112, the short arm 130, and the interior surface 180 of the catheter hub, the friction is overcome and the tip protector 100 disengages from the catheter hub.

FIG. 14 shows the tip protector 100 removed from the catheter hub 174 and the distal wall 150 blocking the needle tip. As the tip protector incorporates two side walls 110A, 110B, and a deflector plate 112, the tip protector covers about three quarters of the circumference of the needle 170 proximate the needle tip. The remaining section of the needle 170 proximate the needle tip 172 is also partly covered by the short arm 130 and the distal blocking section of the first protector body 102. The needle tip is shielded from view or contact. Blood, which may drip from the needle tip, is configured to be caught by one of the walls.

As shown in FIG. 14, if a force is exerted at the distal end of the tip protector near point 189, the needle 170 could pivot away from the shielding provided by the finger section 152 and manipulated so that it re-emerges out the opening 108 of the distal wall 106 of the second protector body 104. Accordingly, in one exemplary embodiment, the dimple or projection 120 on the deflector plate 112 is configured to inhibit or delimit movement of the needle in the event of a direct or incidental force on the tip protector at or near point 189. The projection 120 is configured to prevent movement of the needle tip 172 radially of the finger section 152.

Figure 15:
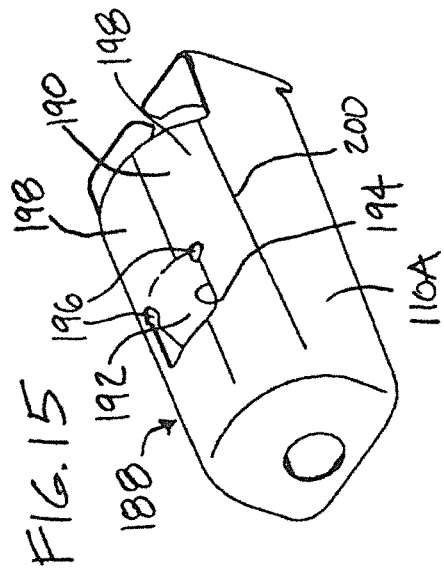
FIG. 15 is a semi-schematic perspective view of an alternative second protector body provided in accordance with aspects of the present invention.

FIG. 15 is a semi-schematic perspective view of a second protector body 188 provided in accordance with aspects of the present invention. The alternative second protector body 188 may cooperate with the first protector body shown in FIGS. 8-10 to form an alternative tip protector. In one exemplary embodiment, the alternative second protector body 188 incorporates a deflector plate 190 comprising a generally curvilinear external surface, a tab 192 formed by making a cut-out 194 on the deflector plate and including two relief points 196. The tab 192, like the projection or dimple 120 on the prior second protector body, is configured to prevent a needle from pivoting out from the tip protector internal space. In one exemplary embodiment, the deflector plate 190 is integrally formed to the side walls 110A and 110B. This can be done, for example, using a deep draw forming process. Still alternatively, the two side walls 110A, 110B and the deflector plate 190 may have a notch of cut-out between them.

In one exemplary embodiment, a least a portion of the curvilinear external surface of the deflector plate 190 is configured to contact the interior surface of a catheter hub when the same is placed therein as part of a catheter assembly. Alternatively, the deflector plate 190 incorporates a flat surface such that only the two side edges 198 with the two side walls 110A, 110B contact the interior surface of the catheter hub or clip housing.

Although limited embodiments of the tip protector and needle devices incorporating the tip protector have been specifically described and illustrated herein, many modifications and variations will be apparent to those skilled in the art. For example, the tip protector described herein may be used in combination with a sleeve on a needle having a bend such as that shown in U.S. Pat. No. 6,585,704 to Luther et al. Alternatively, the tip protector described herein may be used with an outer housing on a needle for use with a syringe, such as that shown in U.S. Pat. No. 6,595,955 to Fergusson et al. Still alternatively, the tip protector described herein may be used with a grip part for sliding the tip protector along a needle, such as that shown in Ser. No. 10/856,315, entitled PROTECTIVE DEVICE FOR AN INJECTION NEEDLE. The foregoing patents and application are expressly incorporated herein by reference as if set forth in full. Accordingly, it is to be understood that the tip protector and its components constructed according to principles of this invention may be embodied other than as specifically described herein. The invention is also defined in the following claims.

What is claimed is:

1. A catheter assembly comprising:
   a catheter hub comprising a wall having an interior wall surface defining an interior cavity;
   a catheter tube attached to and extending distally of the catheter hub, said catheter tube comprising a distal opening;
   a needle, which has a lengthwise axis, a sharpened needle tip, and a crimp, a material build up, a bend or combinations thereof, passing through the catheter hub and the catheter tube with the sharpened needle tip extending distally of the distal opening of the catheter tube in a ready to use position, the needle is attached to a needle hub, which has a nose section at a distal end of the needle hub;
   a tip protector assembly removably held by the interior of the catheter hub and located closer to the nose section than the needle tip in the ready to use position, said tip protector assembly comprising a first protector body located inside an interior of a second protector body;
   wherein the first protector body comprises:
      a proximal wall with a perimeter defining an opening having the needle passing therethrough, a distal wall distal of an end of a first arm, said distal wall being movable distally of the needle tip in a protective position to block the needle tip, said first arm extending distally of the proximal wall from a first end of the proximal wall and extending towards the sharpened needle tip, and a curved arm section located between the distal wall and an elongated portion of the first arm,
      a second arm having a free end extending distally of the proximal wall from a second end of the proximal wall spaced from the first end towards the sharpened needle tip, said second arm having a length between the free end and a proximal end,
   wherein the crimp, the material build up, the bend or the combinations thereof on the needle is configured to engage the perimeter defining the opening on the proximal wall of the first protector body to limit the tip protector assembly from displacing distally off of the needle in a protective position;

wherein the second protector body comprises an interior cavity, a distal end with a distal wall having a first opening and a second opening, said second opening located between the distal end and the proximal end of the second protector body, wherein the needle passes through the first opening but not the second opening in the ready to use position, and wherein the interior cavity of the second protector body is accessible through the second opening from a location external of the second protector body;

wherein the tip protector is configured to space from the nose section of the needle hub in the protective position so that the first protector body and the second protector body block the needle tip; and wherein at least the distal wall of the first protector body and the distal wall of the second protector body are located within the interior cavity of the catheter hub in the ready to use position.

2. The catheter assembly of claim 1, wherein a finger at an end of the distal wall points in a proximal direction.

3. The catheter assembly of claim 1, wherein part of the first protector body is located in the second opening in the ready to use position.

4. The catheter assembly of claim 1, wherein the first arm extends further distally than the second arm.

5. The catheter assembly of claim 1, wherein the first arm crosses the lengthwise axis of the needle in the ready to use position.

6. The catheter assembly of claim 1, wherein the distal wall is located distally of the sharpened needle tip in the protective position to block distal travel of the needle.

7. The catheter assembly of claim 1, wherein part of the first protector body is located in the second opening in the ready to use position.

8. The catheter assembly of claim 1, wherein the tip protector assembly is completely located inside the catheter hub in the ready to use position.

9. A catheter assembly comprising:
a catheter hub comprising a wall having an interior wall surface defining an interior cavity;
a catheter tube attached to and extending distally of the catheter hub, said catheter tube comprising a distal opening;
a needle hub comprising a nose section at a distal end thereof having a needle projecting distally out through the nose section, wherein the needle, which has a lengthwise axis, a sharpened needle tip, and a crimp or a material build up, passes through the catheter hub and the catheter tube with the sharpened needle tip extending distally of the distal opening of the catheter tube in a ready to use position;
a tip protector assembly removably held by the interior wall surface of the catheter hub and located closer to the nose section than the needle tip in the ready to use position, said tip protector assembly comprising a first protector body located inside an interior of a second protector body;
wherein the second protector body comprises a distal end with a distal wall enclosing the distal end and having a first opening formed through the distal wall, a proximal end, and a second opening located between the distal end and the proximal end of the second protector body, wherein the needle passes through the first opening but not the second opening in the ready to use position, and wherein an interior of the second protector body is accessible through the second opening from a location external to the second protector body;

wherein the first protector body comprises:
a proximal wall having a perimeter defining an opening having the needle passing therethrough,
a first arm extending distally of the proximal wall from a first end of the proximal wall and extending towards the sharpened needle tip, a distal wall at an end of the first arm, and a curved arm section between the distal wall and an elongated portion of the first arm,
a second arm, which comprises two spaced apart side edges, extending distally of the proximal wall from a second end of the proximal wall spaced from the first end and extending towards the sharpened needle tip, and wherein the second arm comprises a distal end, a proximal end, and length between the distal end and the proximal end;
wherein the crimp or the material build up is configured to engage the perimeter defining the opening on the proximal wall of the first protector body to limit the tip protector assembly from displacing distally off of the needle in a protective position;
wherein part of the first protector body is located in the second opening of the second protector body; and
wherein at least the distal wall of the first protector body and the distal wall of the second protector body are located within the interior cavity of the catheter hub in the ready to use position.

10. The catheter assembly of claim 9, wherein a finger on the first arm is biased by the needle in the ready to use position.

11. The catheter assembly of claim 9, wherein the distal wall is located distally of the sharpened needle tip in the protective position to block distal travel of the needle.

12. The catheter assembly of claim 9, wherein the first arm extends further distally than the second arm.

13. The catheter assembly of claim 9, wherein the distal wall is of the first protector body is located to a side of the needle and movable distally of the needle tip in the protective position.

14. The catheter assembly of claim 9, wherein at least part of the first protector is located in the second opening in the ready to use position.

15. The catheter assembly of claim 9, wherein the tip protector assembly is completely located inside the catheter hub in the ready to use position.

16. A catheter assembly comprising:
a catheter hub comprising a wall having an interior wall surface defining an interior cavity;
a catheter tube attached to and extending distally of the catheter hub, said catheter tube comprising a distal opening;
a needle hub comprising a nose section at a distal end thereof having a needle projecting distally out through the nose section, wherein the needle, which has a lengthwise axis, a sharpened needle tip, and a crimp or a material build up, passes through the catheter hub and the catheter tube with the sharpened needle tip extending distally of the distal opening of the catheter tube in a ready to use position;
a tip protector assembly removably held in the interior of the catheter hub and located closer to the nose section than the needle tip in the ready to use position, said tip protector assembly comprising a first protector body located inside an interior of a second protector body and both the first protector body and the second protector body are located inside the interior of the catheter hub in the ready to use position;

wherein the second protector body comprises a distal end with a distal wall enclosing the distal end and having a first opening formed through the distal wall, a proximal end, and a second opening located between the distal end and the proximal end of the second protector body, wherein the needle passes through the first opening and part of the first protector body is located in the second opening in the ready to use position and the part of the first protector body extends externally of the second protector body;

wherein the first protector body comprises:

a proximal wall having a perimeter defining an opening having the needle passing therethrough, a first arm extending distally of the proximal wall from a first end of the proximal wall and extending towards the sharpened needle tip, a distal wall at an end of the first arm, and a finger at an end of the distal wall, a second arm, which comprises two spaced apart side edges, extending distally of the proximal wall from a second end of the proximal wall spaced from the first end towards the sharpened needle tip, and wherein the second arm comprises a distal end, a proximal end, and length between the distal end and the proximal end;

wherein the crimp or the material build up is configured to engage the perimeter defining the opening on the proximal wall of the first protector body to limit the tip protector assembly from displacing distally off of the needle in a protective position; and wherein at least the distal wall of the second protector is located within the interior cavity of the catheter hub in the ready to use position.

17. The catheter assembly of claim 16, wherein the finger on the first arm is biased by the needle in the ready to use position.

18. The catheter assembly of claim 16, wherein the distal end of the second arm is spaced from the needle in the ready to use position and the protective position.

19. The catheter assembly of claim 16, wherein the first arm extends further distally than the second arm.

20. The catheter assembly of claim 16, wherein the tip protector assembly is completely located inside the catheter hub in the ready to use position.

21. The catheter assembly of claim 16, wherein a curved arm portion of the first protector is located in the second opening in the ready to use position.

* * * * *